(12) United States Patent
Mahmoud

(10) Patent No.: US 9,803,090 B2
(45) Date of Patent: Oct. 31, 2017

(54) SELF-DISINFECTING SURFACES

(71) Applicant: CRODA INTERNATIONAL PLC, Yorkshire (GB)

(72) Inventor: Hossein Mahmoud, Ede (NL)

(73) Assignee: CRODA INTERNATIONAL PLC (GB)

( * ) Notice: Subject to any disclaimer, the term of this patent is extended or adjusted under 35 U.S.C. 154(b) by 0 days.

(21) Appl. No.: 14/764,623

(22) PCT Filed: Jan. 31, 2014

(86) PCT No.: PCT/EP2014/051970
§ 371 (c)(1),
(2) Date: Jul. 30, 2015

(87) PCT Pub. No.: WO2014/118350
PCT Pub. Date: Aug. 7, 2014

(65) Prior Publication Data
US 2015/0361276 A1    Dec. 17, 2015

(30) Foreign Application Priority Data

Feb. 1, 2013 (EP) ..................................... 13153682
Mar. 6, 2013 (EP) ..................................... 13158039

(51) Int. Cl.
*A01N 33/12* (2006.01)
*C08K 5/19* (2006.01)
(Continued)

(52) U.S. Cl.
CPC ............... *C09D 5/14* (2013.01); *A01N 25/10* (2013.01); *A01N 33/12* (2013.01); *A01N 37/06* (2013.01);
(Continued)

(58) Field of Classification Search
None
See application file for complete search history.

(56) References Cited

U.S. PATENT DOCUMENTS 4,994,199 A * 2/1991 Scardera ............... C07C 217/28
106/18.32
6,194,530 B1 * 2/2001 Klesse .................... A01N 25/10
526/312

(Continued)

FOREIGN PATENT DOCUMENTS

WO          9821253       5/1998
WO      WO 9821253 A1 *  5/1998  ............. A01N 25/10
(Continued)

OTHER PUBLICATIONS

International Search Report for International Application No. PCT/EP2014/051970 dated Mar. 14, 2014.
(Continued)

*Primary Examiner* — Peter A Salamon
(74) *Attorney, Agent, or Firm* — RatnerPrestia

(57) ABSTRACT

The invention relates to an aqueous coating composition comprising a compound having reactive groups A, and a quaternary ammonium compound according to Formula I, II or III

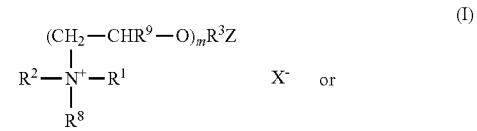
(I)

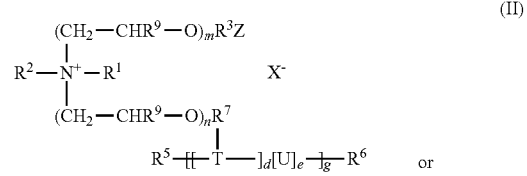

(II)

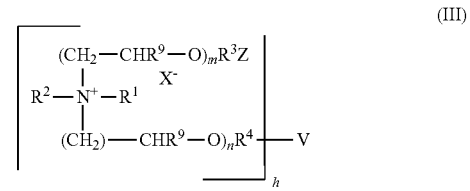

(III)

wherein
$R^1$ is an alkyl, alkenyl, alkylaryl or arylalkyl group having from 5 to 50 carbon atoms;
$R^2$ is a $C_1$-$C_{100}$ hydrocarbyl group, optionally containing heteroatoms;
$R^3$ and $R^4$ are alkylene groups having from 1 to 4 carbon atoms;
$R^5$ and $R^6$ are H or $C_1$-$C_{100}$ hydrocarbyl group, optionally containing heteroatoms;
$R^7$ is a $C_1$-$C_{100}$ hydrocarbyl group, optionally containing heteroatoms;
$R^8$ is a $C_1$-$C_{100}$ hydrocarbyl group, optionally containing heteroatoms;
$R^9$ is H or a methyl group;
Z is a substituent containing at least one reactive group B which is capable of reacting with the reactive group A;
$X^-$ is an anion;
y is 0 or 1;
a is 0 or 1; and the sum of y and a is 1 or 2 and
m is an integer from 1 to 30, preferably between 1 and 10, or between 2 and 6
n is an integer from 0-30, preferably between 1 and 10, or 2 and 6
T is a monomer unit;
U is a monomer unit;
V is a $C_1$-$C_{100}$ hydrocarbyl group, optionally containing hetero atoms;
d is an integer between 1 and 5, preferably 1;
(Continued)

e is an integer between 1 and 1000, preferably between 5 and 100;

g is an integer between 1 and 100, preferably between 2 and 10;

h is an integer between 1 and 5, preferably 2 or 3.

5 Claims, No Drawings

(51) Int. Cl.
- C09D 5/14 (2006.01)
- A01P 1/00 (2006.01)
- A01N 25/10 (2006.01)
- C07C 217/50 (2006.01)
- C09D 5/02 (2006.01)
- C08K 5/00 (2006.01)
- A01N 37/06 (2006.01)
- C07C 271/22 (2006.01)
- C09D 175/04 (2006.01)

(52) U.S. Cl.
CPC .......... *C07C 217/50* (2013.01); *C07C 271/22* (2013.01); *C08K 5/0058* (2013.01); *C08K 5/19* (2013.01); *C09D 5/02* (2013.01); *C09D 175/04* (2013.01); *Y10T 428/31551* (2015.04)

(56) References Cited

U.S. PATENT DOCUMENTS

| 8,093,352 B2 * | 1/2012 | DeSousa | A01N 33/12 424/78.37 |
| 2010/0158853 A1 | 6/2010 | DeSousa | |
| 2011/0160426 A1 | 6/2011 | Greiner | |
| 2013/0195793 A1 | 8/2013 | Schwalm | |
| 2013/0196075 A1 | 8/2013 | Konradi | |

FOREIGN PATENT DOCUMENTS

| WO | 0210244 | 2/2002 | |
| WO | WO 0210244 A2 * | 2/2002 | .......... C08F 290/067 |
| WO | 2008000429 | 1/2008 | |

OTHER PUBLICATIONS

International Preliminary Report on Patentability for International Application No. PCT/GB2013/053247 dated Jun. 23, 2015.

International Preliminary Report on Patentability for International Application No. PCT/EP2014/051970 dated Aug. 4, 2015.

* cited by examiner

SELF-DISINFECTING SURFACES

CROSS REFERENCE TO RELATED APPLICATIONS

This application is the U.S. National Phase application of PCT International Application No. PCT/EP2014/051970, filed Jan. 31, 2014, and claims priority of EP 13153682.3, filed Feb. 1, 2013, and EP 13158039.1, filed Mar. 6, 2014, the disclosures of which are incorporated herein by reference in their entireties for all purposes.

The invention relates to self-disinfecting surfaces, creation of cationic surfaces, an anti-microbial coating, the use of an anti-microbial coating and cationic polymers.

The possibility that bacteria and/or other micro-organisms such as molds and algae accumulate on articles, may form a threat to human health, particularly in the case of bacteria. This problem is particularly prolific in situations where lots of people gather and/or in situations where there are people with a lowered resistance. Such situations occur in, for example, hospitals, nursing homes and care homes for the elderly.

Several ways of tackling the problem of accumulation of micro-organisms on articles are well known in the art, for example manufacturing objects of a material having an anti-microbial effect or treating the article with anti-microbial substances.

Examples of manufacturing objects of a material with an anti-microbial effect are the manufacture of work surfaces for kitchens and packaging materials for food. In these applications, the objects are produced of special materials that have an anti-microbial effect.

Methods of treating existing objects may for example be an air treatment, whereby an anti-microbial substance is distributed in the atmosphere. However, such an approach is bad for the environment in general, and also toxic for humans.

Another known method of treating existing objects provides a different type of solution, namely a paint-like coating with anti-microbial properties that can be applied to existing objects after manufacture, for example suitable coating compositions may comprise water-borne polyurethane dispersions containing an anti-microbial compound.

An anti-microbial substance which is described in the prior art is a quaternary ammonium compound. An example of a quaternary ammonium compound is for instance described in U.S. Pat. No. 8,093,352. In this patent publication polyquaternary ammonium polymers containing polyalkylene oxide groups are described. The quaternary ammonium moieties and polyalkylene oxides are incorporated into the polymer backbone. Another example of a quaternary ammonium compound is described in U.S. Pat. No. 4,994,199. This patent publication discloses antimicrobial amine glycidol compounds which may be used in cleaning compositions or surface coating compositions. The prior art does not describe cured coatings with anti-microbial properties comprising quaternary ammonium compounds. It is a problem in the prior art that resin compositions, that lead to coatings having antimicrobial properties, also show antimicrobial properties as a liquid resin composition. These resin compositions are therefore toxic for the environment and for people handling the resin compositions. At the same time there is a strong need for coatings having antimicrobial properties; such coatings should be present on all kinds of substrates in for example hospitals to prevent spread of bacteria like for example MRSA. Up till now, these coatings have been prepared with the use of toxic resin compositions with all kinds of environmental drawbacks and problems which has also lead to legislative restrictions by governments of different countries.

Another drawback of the prior art is that the resin compositions having antimicrobial activity are cationically stabilized to give a stable dispersion in water. Quaternary ammonium compounds will only give stable dispersions together with cationically stabilized resin dispersions.

Most resin compositions which are present in the prior art (and which do not have antimicrobial properties) are however anionically stabilized. Use of anionically stabilized resin dispersion would give a greater flexibility in design of the resin compositions, and would also lead to improved mechanical properties of the coatings prepared from the anionically stabilized resin compositions.

It is therefore an object to provide a resin composition which has limited antimicrobial properties and limited toxicity which can be applied to a substrate to provide a cured coating on the substrate, which coating provides anti-microbial properties.

It is also an object of the invention to provide anionically stabilized resin compositions comprising cationic compounds, like for example quaternary ammonium compounds, which will render excellent coatings on substrates having good self-disinfecting properties, like for example good antimicrobial properties.

The present invention relates to a process for forming a coating having antimicrobial properties on a substrate comprising the steps of
a) applying a coating composition comprising a quaternary ammonium compound having an alkoxylated substituent having a reactive group on a substrate
b) curing the coating composition to obtain a cured coating,
wherein the reactive group of the alkoxylated substituent has reacted within the cured coating.

Preferably, the alkoxylated substituent comprises ethyleneoxide and/or propyleneoxide units, more preferably between 1 and 30 ethyleneoxide monomeric units. most preferably between 2 and 10 ethyleneoxide monomeric units.

The quaternary ammonium compound preferably comprises a C5-C50 hydrocarbyl chain, more preferably a C10-C20 linear alkyl substituent, most preferably a C12-C15 linear alkyl substituent.

Preferably the coating composition has a low anti-microbial activity, wherein the low anti-microbial activity is defined as less than 20% inhibition of bacterial growth of *pseudomonas aeruginosa*, according to ISO/FDIS 20776-1 (2006); preferably the inhibition of bacterial growth of the *pseudomonas aeruginosa* is less than 10%, most preferably less than 5%.

Preferably the cured coating has a surface charge above $1 \times 10^{15}/cm^2$, preferably of at least $2 \times 10^{15}/cm^2$, more preferably at least $3 \times 10^{15}/cm^2$.

The invention also relates to an aqueous coating composition comprising a compound having reactive groups A, and a quaternary ammonium compound according to Formula I, II or III

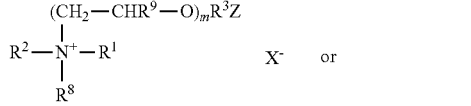

-continued

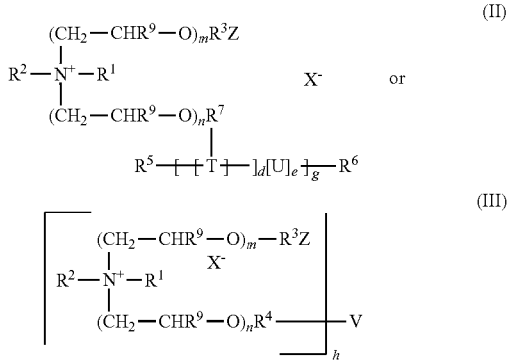

wherein
R¹ is an alkyl, alkenyl, alkylaryl or arylalkyl group having from 5 to 50 carbon atoms;
R² is a $C_1$-$C_{100}$ hydrocarbyl group, optionally containing heteroatoms;
R³ and R⁴ are alkylene groups having from 1 to 4 carbon atoms;
R⁵ and R⁶ are H or $C_1$-$C_{100}$ hydrocarbyl group, optionally containing heteroatoms;
R⁷ is a $C_1$-$C_{100}$ hydrocarbyl group, optionally containing heteroatoms;
R⁸ is a $C_1$-$C_{100}$ hydrocarbyl group, optionally containing heteroatoms;
R⁹ is H or a methyl group;
Z is a substituent containing at least one reactive group B which is capable of reacting with the reactive group A;
X⁻ is an anion;
m is an integer from 1 to 30, preferably between 1 and 10, or between 2 and 6;
n is an integer from 0-30, preferably between 1 and 10, or 2 and 6;
T is a monomer unit;
U is a monomer unit;
V is a $C_1$-$C_{100}$ hydrocarbyl group, optionally containing hetero atoms;
d is an integer between 1 and 5, preferably 1;
e is an integer between 1 and 1000, preferably between 5 and 100;
g is an integer between 1 and 100, preferably between 2 and 10;
h is an integer between 1 and 5, preferably 2 or 3.

The compound having reactive groups A can be a polymer having reactive groups A or a crosslinker having reactive groups A, that can act as a crosslinking agent for the reactive groups B.

The term "polymer" is used herein for a molecule comprising two or more repeating units. In particular it may be composed of two or more monomers which may be the same or different. As used herein, the term includes oligomers and prepolymers. Usually polymers have a number average weight of about 500 g/mol or more, in particular of about 1000 g/mol or more, although the molar mass may be lower in case the polymer is composed of relatively small monomeric units and/or the number of units is relatively low.

Examples of reactive groups A are, for example, hydroxyl, carboxylic acid, urea, acetoacetate, aldehyde, isocyanate, ethyleneimine, anhydride, ester, acrylate, methacrylate, amine, amide, thiol, epoxide or vinyl groups.

For providing a cross-linked network, a polymer having an average number of reactive groups A per molecule of more than 1 is in particular suitable. Preferably, the average number of reactive groups A per molecule is at least 1.2, more preferably at least 1.5, in particular at least 2.0. Preferably the average number of reactive groups A is up to 200 or 64, more preferably in the range of up to 15, in particular in the range of up to 8, more in particular up to 7. However, also a polymer which is free of such reactive groups may be present in the composition.

The coating composition can comprise at least one polymer selected from the group consisting of poly(lactams), in particular polyvinylpyrrolidones; polyurethanes; polyureas; homo- and copolymers of acrylic and methacrylic acid; polyvinyl alcohols; polyvinylethers; maleic anhydride based copolymers; polyesters; vinylamines; polyethyleneimines; polyethylene oxides; poly(carboxylic acids); polyamides; polyanhydrides; polyphosphazenes; cellulosics, in particular methyl cellulose, carboxymethyl cellulose, hydroxymethylcellulose, hydroxypropylcellulose and other polysaccharides, in particular chitosans, hyaluronic acids, alginates, gelatins, chitins, heparins, dextrans; chondroitin sulphates; (poly)peptides/proteins, in particular collagens, fibrins, elastins, albumin; polyesters, in particular polylactides, polyglycolides, polycaprolactones; and polynucleotides.

If a polymer with reactive groups A is present, the amount of polymer in the coating composition is preferably higher than 1 wt % based on the total weight of the coating composition, more preferably higher than 10 wt %, most preferably at least 20 wt %. The amount of polymer in the coating composition is preferably lower than 80 wt % based on the total weight of the coating composition, more preferably lower than 70 wt %, most preferably lower than 60 wt %.

Preferably, the polymer in the coating composition is a polyurethane, polyacrylate, polymethacrylate or a polyurea.

The crosslinker can be, for example, selected from aziridine, carbodiimid, melamine, substituted melamine, melamine derivative, multifunctional alcohol, multifunctional aldehyde, multifunctional amine, multifunctional isocyanate, multifunctional epoxide and combinations thereof. Multifunctional means a functionality of at least 2. Examples of multifunctional isocyanates are for example isophorone diisocyanate and polyisocyanates of MDI and HDI. Examples of commercially available crosslinkers are Denacol® EX810 and Tolonate HDT-LV2.

The crosslinker can be present in the coating composition in an amount that is preferably higher than 0.001 wt % based on the total weight of the coating composition, more preferably higher than 0.01 wt %, most preferably higher than 0.1 wt %. The amount of crosslinker in the coating composition is preferably lower than 20 wt % based on the total weight of the coating composition, more preferably lower than 15 wt %, most preferably lower than 10 wt %. In a preferred embodiment of the present invention the ratio $Q_{AB}$ of the molar amount of reactive groups A and the molar amount of reactive groups B is between 0.1 and 2. Preferably the ratio $Q_{AB}$ is between 0.98 and 1.2. Curing of a coating composition with a ratio $Q_{AB}$ around 1 will result in a cured coating having a low amount of residual reactive groups A or B, and a high crosslink density.

The reactive group B can, for example, be independently selected from a hydroxyl, carboxylic acid, aldehyde, anhydride, ester, ethyleneimine, amine, amide, thiol, epoxide, urea, acetoacetate, isocyanate, acrylate, methacrylate or vinyl group. The reactive group B preferably is a hydroxyl, carboxylate, vinyl, isocyanate, amine or amide group.

The coating composition of the present invention may also contain a polymer having reactive groups B.

Examples of crosslinking reactions between reactive groups A and B in preparing a coating are for example reactions of isocyanates with alcohols, amines, carboxylic acids or urea; reactions of epoxies with amine or carboxylic acids, reactions of acetoacetates with alcohols or isocyanates; reactions of alcohols with ethers; reactions of carbodiimides with carboxylic acids; reactions of aziridines with carboxylic acids; reactions of silanol with alcohols; auto-oxidative reactions; UV initiated crosslinking of acrylic and methacrylic groups.

$R^1$ is an alkyl, alkenyl, alkylaryl or arylalkyl group having from 5 to 50 carbon atoms, preferably from 5 to 25 carbon atoms, more preferably from 10 to 20 carbon atoms. $R^1$ preferably is an alkyl group, more preferably a linear alkyl group and most preferably a linear alkyl group having from 10-15 carbon atoms, whereby a linear $C_{14}$ is most preferred as such an $R^1$ group has an optimum bacterial exterminating effect.

$R^2$ and $R^7$ are a $C_1$-$C_{100}$ hydrocarbyl group, optionally containing heteroatoms. $R^2$ and $R^7$ may preferably be a $C_5$-$C_{50}$ hydrocarbyl group, more preferably $C_{10}$-$C_{20}$ hydrocarbyl group, optionally comprising hetero atoms, for example N, O, P and S. $R^2$ and $R^7$ include but is not limited to branched and unbranched aliphatic hydrocarbyl chains; substituted chains with groups containing heteroatoms, such as S and/or O and/or N; chains containing aliphatic and/or cyclo-aliphatic and/or aromatic groups in the backbone or as substituents; saturated and unsaturated chains. $R^2$ can also be a group that is grafted onto a polymer or copolymerized into a polymer. In one embodiment $R^2$ is a methyl group.

$R^3$ and $R^4$ are alkylene groups having from 1-4 carbon atoms. Examples of alkylene groups are methylene, ethylene, propylene and butylene groups. $R^3$ and $R^4$ can be the same or different.

$R^5$ and $R^6$ are H or a $C_1$-$C_{100}$ hydrocarbyl group optionally containing heteroatoms. $R^5$ and $R^6$ may optionally comprise hetero atoms, for example N, O, P and S. $R^5$ and $R^6$ include but are not limited to branched and unbranched aliphatic hydrocarbyl chains; substituted chains with groups containing heteroatoms, such as S and/or O and/or N; chains containing aliphatic and/or cyclo-aliphatic and/or aromatic groups in the backbone or as substituents; saturated and unsaturated chains.

$R^8$ is a $C_1$-$C_{100}$ hydrocarbyl group optionally containing heteroatoms. $R^8$ may for example contain alkyleneoxide groups, such as for example ethyleneoxide groups, propyleneoxide groups or copolymers of ethyleneoxide and propyleneoxide. $R^8$ may also contain a substituent Z.

In a preferred embodiment of the invention $R^8$ is a $(CH_2CH_2O)_n$—$R^4$—Z fragment $R^9$ is H or a methyl group. Preferably $R^9$ is H, which makes the ($CH_2$—$CHR^9$—O) fragment an ethyleneoxide fragment. It is also possible that the alkyleneoxide fragment comprises mixtures of ethyleneoxide and propyleneoxide fragments.

Z is a substituent containing at least one reactive group B. The substituents Z can be the same or different. The reactive group B is a group that can react with the reactive group A under suitable reaction conditions. The reactive conditions can be for instance room temperature and pressure, a high temperature, catalytic conditions or radiation, for example UV radiation.

At least one Z substituent is present in the quaternary ammonium compound. Preferably, the quaternary ammonium compound comprises 2 Z substituents. In one embodiment, the Z substituent containing the reactive group B may be a $C_5$-$C_{50}$ hydrocarbyl group, preferably a $C_{10}$-$C_{20}$ hydrocarbyl group, optionally comprising hetero atoms, for example N, O, P and S. The substituent includes but is not limited to branched and unbranched aliphatic hydrocarbyl chains; substituted chains with groups containing heteroatoms, such as S and/or O and/or N; chains containing aliphatic and/or cyclo-aliphatic and/or aromatic groups in the backbone or as substituents; saturated and unsaturated chains. In one preferred embodiment, Z is a OH, COOH, vinyl, NH2, acrylate, or methacrylate group.

$R^5$, $T_d$, $U_e$ and $R^6$ represent a polymer backbone of a polyacrylate, polyurethane, polyether, polyester, polysiloxane or other type of polymer.

T is a monomeric unit which is covalently connected with $R^4$ in formula (II). In principle T can be derived by polymerization from any monomer which can be polymerized to a copolymer with other monomers. Examples of T are difunctional ethylenically unsaturated monomers like for example acrylates or methacrylate or vinyl monomer with dual reactivity like for instance glycidylmethacrylate or a isocyanate functional methacrylate.

U is a monomer unit which is derived by polymerization from a monomer that can copolymerize with a monomer that leads to polymeric unit T. Examples of monomers that lead to monomeric units U are ethylenically unsaturated monomers like for example acrylates, methacrylates, vinyl monomer or other monomer capable of reacting in an acrylic polymerization reaction.

V is a $C_1$-$C_{100}$ hydrocarbyl group, optionally containing heteroatoms. V may preferably be a $C_5$-$C_{50}$ hydrocarbyl group, more preferably $C_{10}$-$C_{20}$ hydrocarbyl group, optionally comprising hetero atoms, for example N, O, P and S.

$X^-$ is an anion, for example a sulphate, nitrate, phosphate, acetate or a halogen ion. Preferably, the anion may be a halogen ion, e.g. chlorine, bromine, iodine or fluorine. More preferably $X^-$ is $Cl^-$.

m is 1 or more, preferably 2 or more, more preferably 3 or more and most preferably 4 or more; m is 30 or less, preferably 20 or less, more preferably 10 or less.

A specific and preferred example of a compound according to formula (I) is the compound according to formula (Ia) as described below:

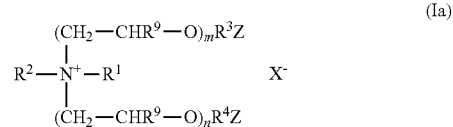

(Ia)

wherein $R^1$, $R^2$, $R^3$, $R^4$, $R^9$, m, n and Z are as defined above.

In one embodiment the invention relates to a compound according to formula (Ia) wherein
$R^9$ is H or methyl, preferably H;
$R^1$ is a linear alkyl group having from 10-15 carbon atoms;
$R^2$ is a $C_1$-$C_{100}$ hydrocarbyl group, optionally containing heteroatoms;
$R^3$ is a C1-C4 alkylene group;
$R^4$ is a C1-C4 alkylene group;
Z is a substituent containing at least one reactive group B which is capable of reacting with the reactive group A;
m is an integer from 1 to 30;
n is an integer from 1 to 30;
X is an anion, preferably a sulphate, nitrate, phosphate, acetate or a halogen ion.

Preferably, the weight average molecular weight (Mw) of the quaternary ammonium compound is at most 10000 g/mol, more preferably at most 5000 g/mol, most preferably 2000 g/mol.

The quaternary ammonium compound can be present in the coating composition in an amount that is preferably higher than 5 wt % based on the weight of the coating composition excluding the carrier liquid, more preferably higher than 7 wt %. The amount of quaternary ammonium compound in the coating composition preferably is lower than 70 wt % based on the total weight of the coating composition excluding the carrier liquid, more preferably lower than 55 wt %, most preferably below 45 wt %.

The coating composition further comprises a carrier liquid in a sufficient amount to disperse or dissolve the other components of the coating composition. The carrier liquid can be present in the coating composition in an amount that is preferably higher than 25 wt % based on the total weight of the coating composition, more preferably higher than 40 wt %, most preferably higher than 45 wt %. The amount of carrier liquid in the coating composition is preferably lower than 90 wt % based on the total weight of the coating composition, more preferably lower than 80 wt %, most preferably lower than 70 wt %. In view of handling properties (low viscosity) and/or in order to facilitate the application of the composition such that a coating with the desired thickness is obtained, the amount of solvent in the composition is preferably relatively high. The carrier liquid may be a single solvent or a mixture. It is chosen such that the polymers can be dissolved or at least dispersed therein. In particular for dissolving or dispersing the polymer well, it is preferred that the carrier liquid is a polar liquid. In particular, a liquid is considered polar if it is soluble in water. The carrier liquid comprises water, and it may contain optionally also an organic liquid soluble in water, preferably an alcohol, more preferably a $C_1$-$C_4$ alcohol, in particular isopropanol and/or ethanol. In case of a mixture, the ratio water to organic solvent, in particular one or more alcohols, may be in the range of about 25:75 to 75:25, in particular 40:60 to 60:40, more in particular 45:55 to 55:45. More preferably the carrier liquid is water. This has the advantage that the coating composition, after application of the coating composition on an article, simply can be dried and no additional measures need to be taken to purify the vapor that is formed during drying.

The liquid coating composition surprisingly has a low anti-microbial activity although there are quaternary ammonium compounds present in the coating composition.

A low anti-microbial activity is defined as less than 20% inhibition of bacterial growth of *pseudomonas aeruginosa*, according to ISO 20776-1. Preferably the inhibition of bacterial growth of the *pseudomonas aeruginosa* is less than 10%, most preferably less than 5%.

The low anti-microbial activity of the coating composition is surprising, since the coating composition comprises substantial amounts of quaternary ammonium ions. Without wanting to be bound by theory, it is believed that the quaternary ammonium ions are shielded from the environment when present in the aqueous coating composition. After curing the coating composition, the coated substrates do show a high antimicrobial activity against the bacteria, like *pseudomonas aeruginosa*, MRSA, *E. coli* and many others.

The anti-microbial activity of the coating composition was quantitatively determined in accordance with the principle of the absorption method, as recorded in the standard method of ISO 20776-1 (2006)(minimal inhibitory concentration (MIC) assay): ""Clinical laboratory testing and in vitro diagnostic test systems—Susceptibility testing of infectious agents and evaluation of performance of antimicrobial susceptibility test devices—Part 1: Reference method for testing the in vitro activity of antimicrobial agents against rapidly growing aerobic bacteria involved in infectious diseases". This method is described in detail in the experimental section below.

The coating composition can also contain other additives, for example pigments, fillers, crosslink inititiators, plasticizers, defoaming agents, surfactants and photostabilizers.

The present invention also relates to an anti-microbial coating that is prepared by
a) applying a waterbased liquid coating composition as defined above, having a low anti-microbial activity as determined according to ISO/FDIS 20776-1 (2006), on a substrate; and
b) curing and drying the liquid coating composition to obtain the anti-microbial coating on the substrate.

The amount of quaternary ammonium compound in the coating necessary to kill bacteria is related to the surface charge density of the cured coating, that is caused by the positively charged nitrogen atom of the quaternary ammonium compound. Immobilized quaternary ammonium compounds in the cured coating have a clear antimicrobial effect when the surface charge on the coatings is above of $1 \times 10^{15}$/cm². Better results are obtained when surface charge is at least $2 \times 10^{15}$/cm², best results are obtained when the surface charge is at least $3 \times 10^{15}$/cm². It is generally viewed that substrates are clearly killing bacteria when the positive charge density is above a well-defined threshold. For this type of immobilized quaternary ammonium compounds it was found that the threshold of the cationic surface density is $3 \times 10^{15}$ charge/cm². A method to determine the surface charge density of cured coating films is stated in the examples.

The invention also relates to quaternary ammonium compounds according to formula (II) or Ill,

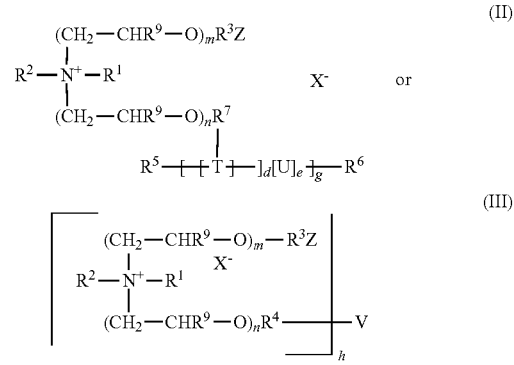

wherein
$R^1$ is an alkyl, alkenyl, alkylaryl or arylalkyl group having from 5 to 50 carbon atoms;
$R^2$ is a $C_1$-$C_{100}$ hydrocarbyl group, optionally containing heteroatoms;
$R^3$ and $R^4$ are alkylene groups having from 1 to 4 carbon atoms;
$R^5$ and $R^6$ are H or $C_1$-$C_{100}$ hydrocarbyl group, optionally containing heteroatoms;
$R^7$ is a $C_1$-$C_{100}$ hydrocarbyl group, optionally containing heteroatoms;

R⁹ is H or a methyl group;

Z is a substituent containing at least one reactive group B which is capable of reacting with the reactive group A;

X⁻ is an anion;

y is 1;

m is an integer from 1 to 30, preferably between 1 and 10, or between 2 and 6 n is an integer from 0-30, preferably between 1 and 10, or 2 and 6

T is a monomer unit

U is a monomer unit

V is a $C_1$-$C_{100}$ hydrocarbyl group, optionally containing heteroatoms;

d is an integer between 1 and 5, preferably 1;

e is an integer between 1 and 1000, preferably between 5 and 100 g is an integer between 1 and 100, preferably between 2 and 10 h is an integer between 1 and 5, preferably 2 or 3.

In one embodiment the quaternary ammonium compound is a compound according to formula (IV)

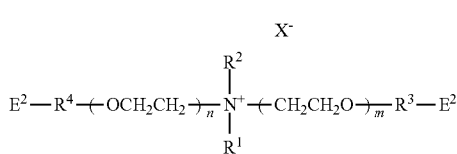

IV wherein $R^1$, $R^2$, $R^3$, $R^4$ are as defined above; m is an integer from 1 to 30; n is an integer from 1-30; m+n is from 2 to 60; $E^2$ is a carboxylate group.

In another embodiment, the quaternary ammonium compound is a compound according to formula (IV), wherein $R^1$, $R^2$, $R^3$, $R^4$ are as defined above; m is an integer from 1 to 30; n is an integer from 1 to 30; m+n is from 10 to 60; and $E^2$ is chosen from the group consisting of acrylate, methacrylate or vinyl groups.

The coating composition can be applied on an article as a thin film in any way known to a person skilled in the art. For example by spraying, dipping, brushing, flooding, bar coating, roll coating, electronic depositing, electrostatic spraying, electroplating, vacuum treatment, pressure treatment or combinations thereof. The anti-microbial coating is obtained by curing the liquid coating composition. The term "to cure" includes any way of treating the coating composition such that it forms a firm or solid coating. In particular, the term includes a treatment whereby the polymer further polymerizes and/or is cross-linked, such that it forms a cross-linked polymer. In general, curing may be carried out by using heat or light; in particular UV, visible or IR light. When curing is performed at an elevated temperature a temperature up to 100° C., preferably up to 150° C. can be used. Curing can be performed in the presence of a photo-initiator or a catalyst. Preferably, the coating is cured at a temperature between 0 and 100° C.

The present invention further relates to articles comprising an anti-microbial coating wherein the surface of the coating contains quaternary ammonium groups having at least one C5-C50 pendant alkyl chain, preferably a C10-C20 linear alkyl chain and at least one alkoxy substituent, which is at one end covalently bound to the nitrogen of the ammonium group and at the other covalently bound to the coating. Such articles are, for example working surfaces in hospitals, elderly homes nursing homes or any other public space, e.g. airports or train stations; medical devices; surgical instruments; articles used in the food industry, e.g. food packaging; swimming pools; ship industry (anti-fouling); keyboards, mobile phones (gsm) and doorknobs. The anti-microbial coatings according to the present invention are preferably used as a coating on a medical device. Examples of medical devices are catheters (both cardiovascular and urinary), guidewires, stents, tongue depressors, stethoscopes, surgical gloves, otoscopes, syringes, thermometers and blood pressure meters. More preferably the anti-microbial coating is used as a coating on a catheter.

The invention will hereafter be described in detail in the examples, without being limited to the contents of the examples.

EXAMPLES

Example 1

Formation of a Quaternary Ammonium Compound According to Formula (I) and a Polymer According to Formula (II)

An amount of 50.00 grams of cocoalkylmethyl[polyoxyethylene (13)]ammonium chloride according to formula (V)

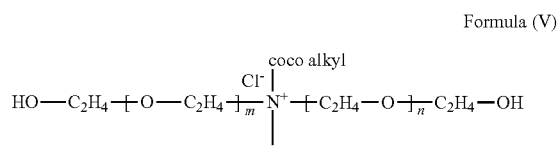

Formula (V)

wherein m+n=13 and a cocoalkyl group is a blend of mainly $C_{12}$ to $C_{14}$ linear alkyl chains, was mixed with 5.54 grams of succinic anhydride (molar ratio 1:2), dissolved in 20.0 grams acetone and heated up to 50° C. for 8 hour in a reaction vessel equipped with a condenser, thermometer and dropping funnel. The progress of the reaction is monitored using acid value titration. The reaction was completed when the acid value no longer decreased. A complex according to formula (VI) has been formed (which is a specific example of a compound according to formula (I)).

Formula (VI)

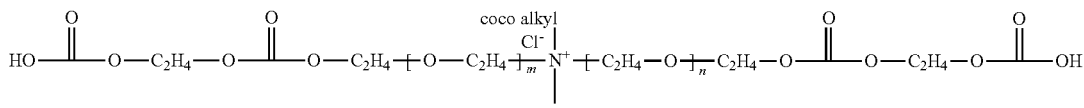

The mixture was cooled to 40° C. and glycidyl methacrylate (8.59 grams) and butyl methacrylate (4.30 grams) are slowly added. The ratio of glycidyl methacrylate to ethoxylated cocoalkyl ammonium is 1.1 to 1 moles. The reaction proceeded for 2 hours at 40° C., giving a structure according to formula (VII) (which is a specific compound to formula (I)). Subsequently, triethylamine (5.5 grams) and water (110.00 grams) were added.

The antimicrobial activity of the compound was determined in the so-called 'minimal inhibitory concentration' (MIC-) assay.

Formula (VII)

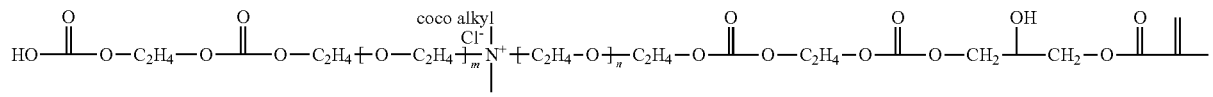

The mixture was diluted to 25% solid content using demi water and heated to 60° C. A nitrogen inlet was added to the reaction vessel. A redox polymerization reaction was carried out using sodium formaldehyde sulfoxylate (0.38 grams) and tertiair butyl hydroxyl peroxide (0.42 grams) as redox couple under a progressive flow of nitrogen. After one hour at 60° C. the mixture was cooled to room temperature. The obtained polymer has a structure according to formula (VIII). Acetone was removed from the emulsion by using a rotary evaporator.

With this test the AM compound can be evaluated for use as an in-can preservative for paints etc.

The anti-microbial activity of the polymers was quantitatively determined in accordance with the principle of the absorption method, as recorded in the standard method of ISO 20776-1: ""Clinical laboratory testing and in vitro diagnostic test systems—Susceptibility testing of infectious agents and evaluation of performance of antimicrobial susceptibility test devices—Part 1: Reference method for testing the in vitro activity of antimicrobial agents against Formula (VIII)

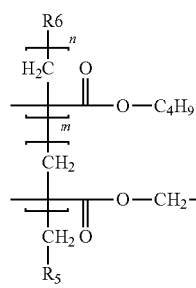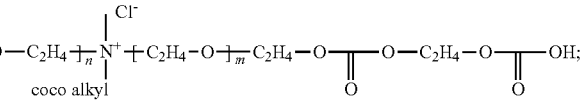

random blockcopolymer, a specific example of a compound according to formula (II).

Example 2

Preparation of Coating Compositions

The emulsion according to Example 1 was diluted with demineralized water up to a solid content of 20 wt %. Afterwards, the emulsion was neutralized using an amine neutralizing agent, preferably triethylamine, to a pH of 8.5±0.1. After neutralization, the emulsion was added dropwise to a polyurethane (PU) dispersion; SYNTEGRA® YA 500 available from Dow Chemical.

Different coating compositions have been prepared by mixing the neutralized emulsions with the PU-dispersion and with 7.5% (m/m) carbodiimide crosslinking agent in ratios as described in table 2.

Formation of the Coating

The different coating compositions (see table 2 for the ratio of the components) have been applied on a glass substrate in a thickness of 120 μm using a laboratory test applicator (TQC VF 2146 baker applicator). After the application of the coating composition, the coating composition was cured at 70° C. for 30 minutes to prepare the coating.

Example 3

Test Procedure for Determination of Antimicrobial Properties of the Coating Composition The anti-microbial properties of the coating composition were tested according ISO/FDIS 20776-1 (2006). This method is described hereafter.

rapidly growing aerobic bacteria involved in infectious diseases". The test was carried out with the gram negative bacteria *Pseudomonas aeruginosa* (BM 179).

After 24 hours of contact at 37° C., the number of surviving organisms was determined and the anti-microbial activity of the polymer samples could be calculated.

The starting concentration of the liquid coating of Example 2 in water was 3%. After dilution (1:1) in Brain Heart Infusion (BHI) medium, 200 μl was applied in the first column of a 96-well plate (Corning 3596) subsequently 100 μl 1:1 diluted liquid coating was three times diluted. The end concentration of the liquid coating in the wells was resp. 1.5, 0.75, 0.375 and 0.188%.

Columns 6 and 12 were used as blank; columns 5 and 11 for 100% growth.

The 96-well plates were closed and sealed with autoclave tape and subsequently packed in aluminum foil. After incubation at 37° C. (timed at T24), the number of the bacteria in the wells was determined with a Tecan Reader by measurement of the OD600.

The density of the used test organism was determined by titration and plating on Tryptic Soy Agar (TSA) base. These TSA sheets were incubated overnight at 35° C., where upon the number of multiplied colonies was counted.

| | % growth inhibition |
|---|---|
| concentration of coating in water | *P. aeruginosa* (24 hours) |
| 1.5% | 15 |
| 0.75% | 20 |

-continued

| % growth inhibition | |
|---|---|
| concentration of coating in water | P. aeruginosa (24 hours) |
| 0.375% | 6 |
| 0.188% | 9 |

In all experiments bacterial growth was clearly visible. From table above it can be concluded that the coating of example 2 showed no antimicrobial activity against the Gram-negative bacteria *Pseudomonas aeruginosa* (BM179).

Example 4

Test Procedure for Determination of Antimicrobial Properties

For determination of the antimicrobial properties of the coatings a test was applied according the Japanese standard JIS L 1902 (2002). In brief, one of the coating formulations described in example 2 was applied to a microscopy glass substrate and cured for 24 hrs at 70° C. Meanwhile, suspensions of *P. aeruginosa, E. Coli* and *S. Aureus* were grown in BHI medium for 24 hrs at 37° C., resulting in suspensions of at least $10^5$-$10^6$ bacteria/ml. Afterwards, the cured coating plates were contaminated with bacteria via dropping 100 μL of the suspension on the coating. The droplet was covered by a microscopy glass-slide and incubated at 37° C. for 24 hrs. After incubation, the glass slide was removed and the suspension droplet was diluted with another 100 μL of fresh BHI medium. In the case of *E. Coli* and *P. aeruginosa*, the droplet was plated out on a freshly prepared agar plate containing tryptic soy agar which was able to stain colonies of *E. Coli* and *P. aeruginosa* specifically. In the case of *S. Aureus* the droplet was poured in an empty petri-dish and mixed with freshly sterilized tryptic soy agar, which was able to stain *S. Aureus* colonies specifically. The plates were incubated at 37° C. for 24 hrs, after which the colonies were counted to determine the antimicrobial effectivity of the coating. The tests were carried out in duplo. The results are shown in Table 2. The given weight percentages are based on total weight of the solids present in the coating formulation. The percentage inhibition is the amount of inhibition of bacteria growth on the coating relative to a coating wherein no quaternary ammonium component was present.

The results in Table 2 clearly show that an effective antimicrobial coating is obtained when the amount of quaternary ammonium compound in the coating formulation is 15 or preferably 20% weight % or higher relative to the weight of the total amount of solids in the coating formulation.

Example 5

Test Procedure for Determination of the Surface Charge Density

The density of quaternary ammonium groups on surfaces was measured as the amount of fluorescein bound on the surface of the coatings. The coating compositions from Example 2 were applied on glass slides (test surface 1×1 $cm^2$) and placed in a tube containing 10 mL of a 1% (wt) solution of sodium salt fluorescein in distilled water for 10 minutes. The samples were removed from the fluorescein solution and were extensively rinsed with distilled water and placed in 3 mL of 0.1% solution of cetyltrimethylammonium chloride in a fresh tube. Subsequently, the samples were shaken for 20 minutes at 300 rpm on an orbital shaker to desorb the dye. The absorbance of the resultant aqueous solution was measured at 501 nm after adding 1 ml of 100 mM PBS (phosphate buffered saline) (pH 8).

The amount of fluorescein bound to quaternary ammonium groups on the surface of the coating was calculated using a value of 77 mM–1/cm as the extinction coefficient. The number of quaternary ammonium units on the coating surface was determined by using a 1:1 fluorescein to accessible quaternary ammonium ratio. Table 3 shows the results as previously presented in table 2 complemented with the measured mole cationic groups accessible at the coating surface. The surface charge per $cm^2$ was calculated by multiplying the surface charge with the Avogadro constant $(6.022*10^{23}\ mol^{-1})$.

TABLE 3

| | Inhibition % of *E. Coli.* | Inhibition % of MRSA | Accessible cationic groups [mol $N^+$/$cm^2$] | Surface charge/$cm^2$ |
|---|---|---|---|---|
| C4.1 | <1% | <1% | — | — |
| C4.2 | 20% | 35% | — | — |
| C4.3 | 35% | 55% | $1.3 \times 10^{-06}$ | $0.8 \times 10^{15}$ |
| 4.4 | 60% | 75% | $2.4 \times 10^{-06}$ | $1.4 \times 10^{15}$ |

TABLE 2

| | Formulation | | | | | |
|---|---|---|---|---|---|---|
| Exp | Syntegra ® YA 500 (wt %) | quaternary ammonium compound (wt %) | carbodiimide crosslinker (wt %) | Inhibition % of *E. Coli.* | Inhibition % of *P. aeruginosa.* | Inhibition % of MRSA. |
| C4.1 | 0 | 0 | 0 | <1% | <1% | <1% |
| C4.2 | 80 | 0 | 20 | 20% | 20% | 35% |
| C4.3 | 80 | 10 | 10 | 35% | 35% | 55% |
| 4.4 | 75 | 15 | 10 | 60% | 60% | 75% |
| 4.5 | 70 | 20 | 10 | >98% | >98% | >99% |
| 4.6 | 65 | 25 | 10 | >99% | >99% | >99% |
| 4.7 | 60 | 30 | 10 | >99% | >99% | >99% |
| 4.8 | 55 | 35 | 10 | >99% | >99% | >99% |
| 4.9 | 50 | 40 | 10 | >99% | >99% | >99% |

TABLE 3-continued

| | Inhibition % of E. Coli. | Inhibition % of MRSA | Accessible cationic groups [mol N$^+$/cm$^2$] | Surface charge/cm$^2$ |
|---|---|---|---|---|
| 4.5 | >98% | >99% | 3.7 × 10$^{-06}$ | 2.2 × 10$^{15}$ |
| 4.6 | >99% | >99% | 5.3 × 10$^{-06}$ | 3.2 × 10$^{15}$ |
| 4.7 | >99% | >99% | 7.2 × 10$^{-06}$ | 4.3 × 10$^{15}$ | urethane acrylate (equivalent ratio 2:1) and 0.01 grams of DBTL (dibutyltin dilaurat) and heated up to 65° C. for 2 hours in a reaction vessel equipped with a condenser and thermometer. The progress of the reaction was monitored by determining the NCO-number. The reaction was stopped when the NCO number was below 0.1%. The reaction resulted in the structure according to formula (VIII). Finally, distilled water was added to obtain a solid matter content of 50%.

Formula (VIII)

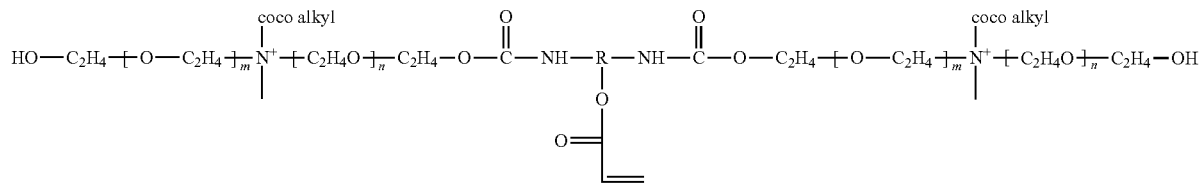

TABLE 3-continued

| | Inhibition % of E. Coli. | Inhibition % of MRSA | Accessible cationic groups [mol N$^+$/cm$^2$] | Surface charge/cm$^2$ |
|---|---|---|---|---|
| 4.8 | >99% | >99% | 9.3 × 10$^{-06}$ | 5.6 × 10$^{15}$ |
| 4.9 | >99% | >99% | 1.2 × 10$^{-05}$ | 7.0 × 10$^{15}$ |

The results in Table 3 show clearly that an effective antimicrobial coating can be obtained when the surface charge on the coatings is above of 1×10$^{15}$/cm$^2$, better results when surface charge is at least 2×10$^{15}$/cm$^2$, best results are obtained when the surface charge is the material specific threshold of at least 3×10$^{15}$/cm$^2$.

Example 6

Assessment of Leaching of Antimicrobial Substances from Coatings of Example 2

The coating of Example 2 was applied on glass in a coating thickeness of 120 μm using a laboratory test applicator (TQC VF 2146 baker applicator). After drying the coating was removed from the glass and cut into little pieces. About 0.6 to 0.7 grams of coating pieces were extracted in a soxhlet with 150 ml ultra-pure water (Milli-Q) for 16 hours. Samples of the extracts were diluted 10 times with eluent and injected with flow injection in a Q-TOF™ hybrid instrument Flow injection electrospray Mass Spectrometer with standard Z-spray™ interface and an Alliance liquid chromatograph type 2690 (eluent: H$_2$O:CH$_3$CN 1:1 with 0.2% formic acid; flow 20 μl/min.). From the analyses it was concluded that no quaternary ammonium compounds were extracted from the samples. The detection limit of quaternary ammonium compounds is <1 ppm, so the extractable amount of quaternary ammonium compounds from the coatings is lower than 0.2%.

Example 7

Formation of a Quaternary Ammonium Compound Carrying Free Acrylic Groups According to Formula (III)

An amount of 59.6 grams of ethoxylated cocoalkyl methyl ammonium chloride (m+n=13 moles) was mixed with 10.0 grams of Desmolux D 100, an isocyanate bearing Example 8

Formation of a PUR-coating of the QAC from Example 7

To 50 grams of OH functional acrylate dispersion AC 27401 (Alberdingk Boley) was mixed thoroughly with 20 grams of the 50% solid QAC solution comprising the compound of Example 7 and 41 grams of hydrophilic aliphatic polyisocyanate Bayhydur XP 2547 (Bayer). A coating was applied on a glass substrate using a laboratory test applicator (TQC VF 2146 baker applicator). After the application, the coating was cured at 50° C. for 30 minutes. The resulting coating layer was a clear transparent, flexible and shiny coherent layer.

Example 9

Formation of a Waterborne UV-coating of the QAC from Example 7

To 50 grams of UV-Curable Polyurethane/Acrylic Copolymer Dispersions LUX 560 VP (Alberdigk), 1.25 grams of photo-initiator Irgacure 500 (BASF) and 15 grams of the 50% QAC solution (example 7) were added under stirring.

The coating was applied on a glass substrate using a laboratory test applicator (TQC VF 2146 baker applicator). After the application the coating dried for 10 minutes at 40° C. in a stove and subsequently cured in 2 passes of 5 seconds each with a Decorad handheld lamp type D03.

The cured coating layer was a transparent, uniform, leathery tough and shiny coherent layer.

The invention claimed is:
1. A process for forming a coating having antimicrobial properties on a substrate comprising the steps of:
a. applying a coating composition comprising a quaternary ammonium compound having an alkoxylated substituent having a reactive hydroxyl group according to formula (Ia), (II), or (III) to a substrate, and
b. curing the coating composition to obtain a cured coating,
wherein the reactive hydroxyl group of the alkoxylated substituent has reacted within the cured coating,

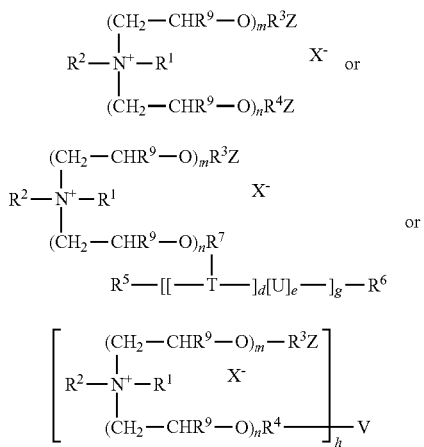

wherein:
R¹ is an alkyl, alkenyl, alkylaryl or arylalkyl group having from 5 to 50 carbon atoms;
R² is a $C_1$-$C_{100}$ hydrocarbyl group, optionally containing heteroatoms;
R³ is a $C_1$-$C_4$ alkylene group;
R⁴ is a $C_1$-$C_4$ alkylene group;
R⁵ and R⁶ are H or $C_1$-$C_{100}$ hydrocarbyl group, optionally containing heteroatoms;
R⁷ is a $C_1$-$C_{100}$ hydrocarbyl group, optionally containing heteroatoms;
R⁹ is H or methyl;
Z is OH;
X⁻ is an anion;
m is an integer from 1 to 30;
n is an integer from 1 to 30; and
T is a monomer unit;
U is a monomer unit;
V is a $C_1$-$C_{100}$ hydrocarbyl group, optionally containing hetero atoms;
d is an integer between 1 and 5;
e is an integer between 1 and 1000;
g is an integer between 1 and 100;
h is an integer between 1 and 5.

2. The process according to claim 1, wherein R⁹ is H.

3. The process according to claim 1, wherein R¹ is a linear alkyl group having from 10 to 15 carbon atoms.

4. The process according to claim 1, wherein the coating composition has a low anti-microbial activity, wherein the low anti-microbial activity is defined as less than 20% inhibition of bacterial growth of pseudomonas aeruginosa, according to ISO/FDIS 20776-1 (2006).

5. The process according to claim 1, wherein the cured coating has a surface charge above $1 \times 10^{15}$ /cm².

* * * * *